United States Patent
Henschel et al.

(10) Patent No.: US 12,290,693 B2
(45) Date of Patent: May 6, 2025

(54) FEEDTHROUGH HEADER ASSEMBLY AND DEVICE INCLUDING SAME

(71) Applicant: Medtronic, Inc., Minneapolis, MN (US)

(72) Inventors: Mark E. Henschel, Phoenix, AZ (US); Andrew J. Ries, Lino Lakes, MN (US); Songhua Shi, Tempe, AZ (US); Jemmy Sutanto, Scottsdale, AZ (US); Lea Ann Nygren, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 17/587,676

(22) Filed: Jan. 28, 2022

(65) Prior Publication Data
US 2022/0241598 A1    Aug. 4, 2022

Related U.S. Application Data

(60) Provisional application No. 63/143,996, filed on Feb. 1, 2021.

(51) Int. Cl.
*A61N 1/375*   (2006.01)
*H01R 12/52*   (2011.01)
*H01R 43/20*   (2006.01)

(52) U.S. Cl.
CPC .......... *A61N 1/3754* (2013.01); *A61N 1/3758* (2013.01); *H01R 12/52* (2013.01); *H01R 43/205* (2013.01); *A61N 1/37512* (2017.08)

(58) Field of Classification Search
CPC ............... A61N 1/3754; A61N 1/3758; A61N 1/37512; A61N 1/39622; A61N 1/3756; H01R 12/52; H01R 43/205
See application file for complete search history.

(56) References Cited

U.S. PATENT DOCUMENTS 5,595,514 A * 1/1997 Romano .............. H01R 13/521
                                                29/874
6,999,818 B2   2/2006 Stevenson et al.
(Continued)

FOREIGN PATENT DOCUMENTS

WO     2018/140623     8/2018

OTHER PUBLICATIONS

International Search Report and Written Opinion for PCT/US2022/014484, mailed May 17, 2022; 11 pages.

*Primary Examiner* — Catherine M Voorhees
(74) *Attorney, Agent, or Firm* — Mueting Raasch Group

(57) ABSTRACT

Various embodiments of an electronics module and an implantable medical device that includes such module are disclosed. The module includes a feedthrough header assembly having a conductive header that includes a conductive inner surface, an outer surface, and a contact disposed on the inner surface and electrically connected to the header; and a feedthrough pin disposed within a via that extends through the header. The module further includes an electronic layer having a substrate and an electronic component disposed on or within the substrate. The electronic component is electrically connected to the contact of the conductive header such that the electronic component is electrically connected to the header. A major surface of the substrate of the electronic layer faces the conductive inner surface of the header without any intervening nonconductive layers disposed between the major surface of the substrate and the conductive inner surface of the header.

20 Claims, 11 Drawing Sheets

(56) References Cited

U.S. PATENT DOCUMENTS

| | | | |
|---|---|---|---|
| 7,061,949 B1* | 6/2006 | Zhou | H01S 5/02257 |
| | | | 372/36 |
| 8,659,870 B2 | 2/2014 | Brendel et al. | |
| 9,014,808 B2 | 4/2015 | Stevenson et al. | |
| 10,029,107 B1* | 7/2018 | Webb | A61N 1/3756 |
| 10,124,559 B2 | 11/2018 | Sandlin et al. | |
| 2011/0190842 A1 | 8/2011 | Johnson et al. | |
| 2017/0080239 A1 | 3/2017 | Seitz et al. | |
| 2019/0030346 A1 | 1/2019 | Li et al. | |
| 2020/0155860 A1* | 5/2020 | Keller | A61N 1/3756 |
| 2021/0121705 A1 | 4/2021 | Ries et al. | |
| 2021/0187307 A1* | 6/2021 | Ries | A61N 1/3754 |
| 2024/0055159 A1* | 2/2024 | Shanahan | H01B 17/305 |

\* cited by examiner

FEEDTHROUGH HEADER ASSEMBLY AND DEVICE INCLUDING SAME

RELATED PATENT APPLICATION

This application claims the benefit of U.S. Provisional Patent Application Ser. No. 63/143,996, filed on Feb. 1, 2021, which is incorporated by reference herein in its entirety.

TECHNICAL FIELD

This disclosure generally relates to a feedthrough header assembly and in particular an implantable medical device that includes the feedthrough header assembly.

BACKGROUND

Implantable medical devices such as an implantable pacemaker can deliver pacing pulses to a patient's heart and monitor conditions of the patient's heart. In some examples, the implantable pacemaker includes a pulse generator and one or more electrical leads. The pulse generator may, for example, be implanted in a small pocket in the patient's chest. The electrical leads can be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at the target site. The pulse generator may provide electrical stimulation to the target site and/or monitor cardiac electrical activity at the target site via the electrodes.

Other implantable pacemakers are configured to be implanted entirely within a chamber of the heart. Such pacemakers can be referred to as intracardiac pacing devices or leadless pacing devices and can include one or more electrodes on their outer housings to deliver therapeutic electrical signals and/or sense intrinsic depolarizations of the heart. Such pacemakers can be positioned within or outside of the heart and, in some examples, can be anchored to a wall of the heart via a fixation mechanism.

SUMMARY

The techniques of this disclosure generally relate to a feedthrough header assembly and an electronics module that utilizes such feedthrough header assembly. The electronics module can include a feedthrough header assembly and an electronic layer. The assembly can include a conductive header that includes a conductive inner surface and a contact disposed on the inner surface and electrically connected to the header. The assembly can also include a feedthrough pin that is electrically isolated from the header. The electronic layer can include a substrate and an electronic component disposed on or within the substrate, were the electronic component is electrically connected to the contact of the conductive header. A major surface of the substrate of the electronic layer faces the conductive inner surface of the header without any intervening nonconductive layers disposed between the major surface of the substrate and the conductive inner surface of the header. The feedthrough pin extends through the dielectric substrate and the header and beyond an outer surface of the header while maintaining isolation from the header.

In one example, aspects of this disclosure relate to an electronics module that includes a feedthrough header assembly. The assembly includes a conductive header having a conductive inner surface, an outer surface, and a contact disposed on the inner surface and electrically connected to the header; and a feedthrough pin disposed within a via that extends through the header between the inner surface and the outer surface of the header. The feedthrough pin is electrically isolated from the header and includes a first end adjacent to the inner surface of the header and a second end adjacent to the outer surface of the header. The electronics module further includes an electronic layer having a substrate and an electronic component disposed on or within the substrate. The electronic component is electrically connected to the contact of the conductive header such that the electronic component is electrically connected to the header. A major surface of the substrate of the electronic layer faces the conductive inner surface of the header without any intervening nonconductive layers disposed between the major surface of the substrate and the conductive inner surface of the header.

In another example, aspects of this disclosure relate to an implantable medical device that includes a power source and an electronics module electrically connected to the power source. The electronics module includes an electronic layer and a feedthrough header assembly electrically connected to the electronic layer. The electronic layer includes a substrate and an electronic component disposed on the substrate. Further, the feedthrough header assembly includes a conductive header having a conductive inner surface, an outer surface, and a contact disposed on the inner surface and electrically connected to the header; and a feedthrough pin disposed within a via that extends through the header between the inner surface and the outer surface of the header. The feedthrough pin is electrically isolated from the header and includes a first end adjacent to the inner surface of the header and a second end adjacent to the outer surface of the header. The electronic component is connected to the contact of the conductive header such that the electronic component is electrically connected to the header. Further, a major surface of the substrate of the electronic layer faces the conductive inner surface of the header without any intervening nonconductive layers disposed between the major surface of the substrate and the conductive inner surface of the header.

In another example, aspects of this disclosure relate to a method that includes disposing a feedthrough pin through a via of a conductive header, where a first end of the feedthrough pin is adjacent to a conductive inner surface of the header and a second end of the feedthrough pin is adjacent to an outer surface of the header. The method further includes disposing a contact on the inner surface of the header such that it is electrically connected to the header; and electrically connecting an electronic component of an electronic layer to the contact such that the electronic component is electrically connected to the header. The electronic component is disposed on or within a substrate of the electronic component. Further, a major surface of the substrate of the electronic layer faces the conductive inner surface of the header without any intervening nonconductive layers disposed between the major surface of the substrate and the conductive inner surface of the header.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to a feedthrough header assembly and an electronics module that utilizes such feedthrough header assembly. The electronics module can include a feedthrough header assembly and an electronic layer. The assembly can include a conductive header that includes a conductive inner surface and a contact disposed on the inner surface and electrically connected to the header. The assembly can also include a feedthrough pin that is electrically isolated from the header. The electronic layer can include a substrate and an electronic component disposed on or within the substrate, were the electronic component is electrically connected to the contact of the conductive header. A major surface of the substrate of the electronic layer faces the conductive inner surface of the header without any intervening nonconductive layers disposed between the major surface of the substrate and the conductive inner surface of the header. The feedthrough pin extends through the header and beyond an outer surface of the header while maintaining isolation from the header.

Typical header assemblies of implantable medical devices can include a feedthrough pin that is electrically connected to an electronics module disposed within a housing of the device. The feedthrough pin can extend from inside the housing and beyond a header that is connected to the housing. Because one or both of the housing or the header can be electrically active, the feedthrough pin is typically electrically isolated from both the header and the housing. An opening in the header and the housing through which the feedthrough pin extends must be sealed such that body fluids and contaminants do not flow into an interior of the housing where they can damage electronic components.

One or more embodiments of the present disclosure can provide a feedthrough header assembly that includes a feedthrough pin that can be connected to an electronics module disposed within a housing of a device, where the feedthrough pin is electrically connected to the module in a reliable manner while efficiently utilizing space within the housing. The feedthrough header assembly can be a solderable component or subassembly that is compatible with various standard surface mount processing and connects to an integrated circuit or die stack in a reliable and volumetrically efficient manner.

Figure 1:
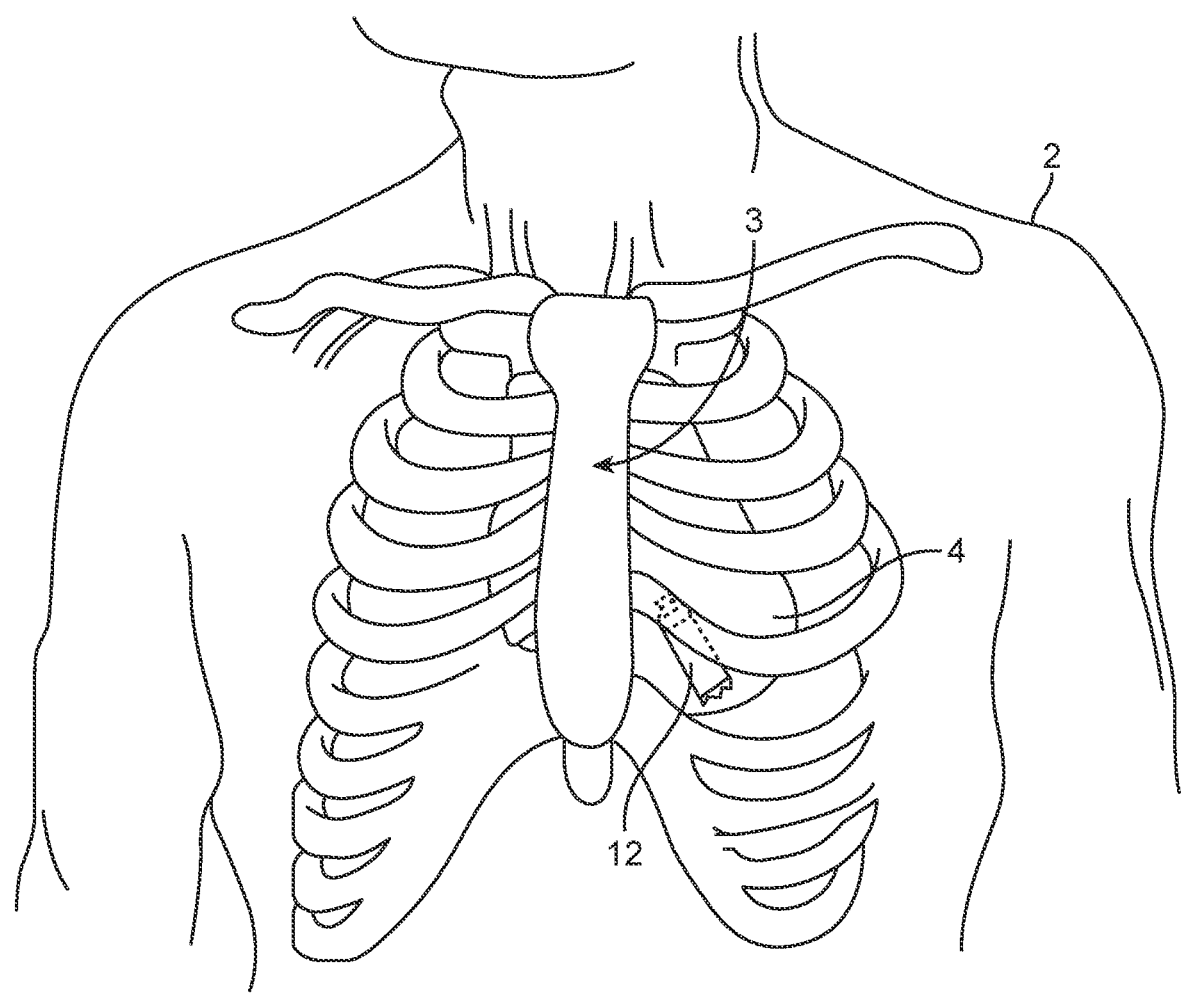
FIG. 1 is a schematic view of one embodiment of an implantable medical device disposed within a body of a patient.

FIG. 1 is a schematic view of one embodiment of an implantable medical device 12 (IMD) disposed within a body of a patient 2. The IMD 12 can include any suitable medical device, e.g., a pacing device, pressure sensing device, cardiac monitor, other physiologic sensor, etc. The IMD 12 can include an arrangement of an electronics module and a feedthrough header assembly as is further described herein. IMD 12 can be, for example, an implantable leadless pacing device that is configured for implantation entirely within one of the chambers of a heart 4 and that provides electrical signals to the heart beneath a sternum 3 via electrodes carried on the housing of the pacing device.

IMD 12 is generally described as being attached within a chamber of the heart 4 as an intracardiac pacing device. In one or more embodiments, IMD 12 can be attached to an external surface of the heart 4 such that the device is disposed outside of the heart but can pace a desired chamber. In one or more embodiments, IMD 12 is attached to an external surface of the heart 4, and one or more components of the device can be in contact with an epicardium of the heart. The IMD 12 is schematically shown in FIG. 1 attached to a wall of a ventricle of the heart 4 via one or more fixation elements (e.g., tines, helix, etc.) that penetrate the tissue. These fixation elements can secure the IMD 12 to the cardiac tissue and retain an electrode (e.g., a cathode or an anode) in contact with the cardiac tissue. IMD 12 can be implanted at or proximate to the apex of the heart. In one or more embodiments, a pacing device may be implanted at other ventricular locations, e.g., on the free-wall or septum, an atrial location, or any location on or within the heart 4.

Figure 2:
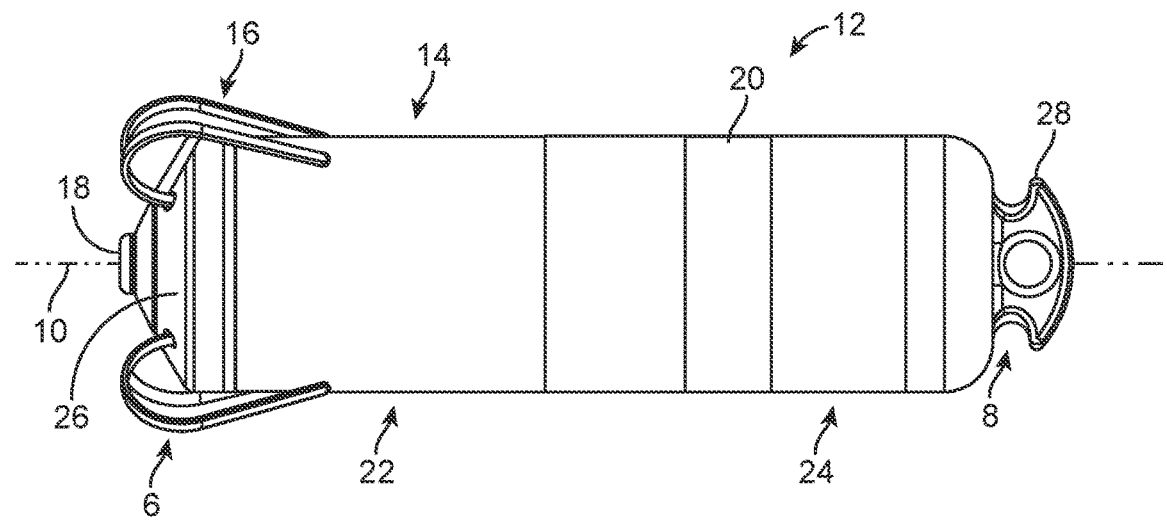
FIG. 2 is a schematic perspective view of the implantable medical device of FIG. 1.

FIG. 2 is a schematic side view of the IMD 12 of FIG. 1. In one or more embodiments, the IMD 12 is adapted to be implanted within a chamber of the heart 4 of the patient 2, e.g., to monitor electrical activity of the heart and/or provide electrical therapy to the heart. In the example shown in FIG. 2, the IMD 12 includes a housing 14, fixation tines 16, and electrodes 18 and 20.

The housing 14 of the IMD 12 can include any suitable dimensions and take any suitable shape or shapes. The housing 14 extends between a first end 6 and a second end 8 along a longitudinal axis 10. In one or more embodiments, the housing 14 can have a cylindrical (e.g., pill-shaped) form factor. In one or more embodiments, the housing 14 includes an elongated tubular housing. Further, the housing 14 can include any suitable material or materials as is further described herein.

The IMD 12 can include a fixation mechanism adapted to fix pacing device 12 to tissue within the body of the patient 2. For example, in the embodiment illustrated in FIG. 2, the IMD 12 includes fixation tines 16 extending from the housing 14 that are adapted to engage with tissue to substantially fix a position of the housing within the patient 2. In one or more embodiments, the fixation tines 16 are adapted to anchor housing 14 to the cardiac tissue such that pacing device 12 moves along with the cardiac tissue during cardiac contractions. Fixation tines 16 can include any suitable material or materials, e.g., a shape memory material (e.g., Nitinol). Although the IMD 12 includes a plurality of fixation tines 16 that are adapted to anchor the device to tissue, in one or more embodiments, the device can be fixed to tissue using other types of fixation mechanisms, such as, but not limited to, barbs, coils, and the like.

Housing 14, also referred to as an elongated housing, houses electronic components of the IMD 12, e.g., sensing circuitry for sensing electrical activity via electrodes 18 and 20 and therapy generation circuitry for delivering electrical stimulation therapy via the electrodes. Electronic components can include any discrete and/or integrated electronic circuit components that implement analog and/or digital circuits capable of producing the functions attributed to the IMD 12 described herein. In one or more embodiments, housing 14 can also house components for sensing other physiological parameters, such as acceleration, pressure, sound, and/or impedance. Although shown with two electrodes 18 and 20, the device 12 can include any suitable number of electrodes disposed in any suitable portion or portions of the housing.

Additionally, the housing 14 can also house a memory that includes instructions that, when executed by processing circuitry housed within housing, cause the IMD 12 to perform various functions attributed to the device herein. In one or more embodiments, the housing 14 can house communication circuitry that enables the IMD 12 to communicate with other electronic devices, such as a medical device programmer. In one or more embodiments, the housing 14 can house an antenna for wireless communication. The housing 14 can also house a power source, such as a battery.

The housing 14 can be hermetically or near-hermetically sealed using any suitable technique or techniques to help prevent fluid ingress into housing. For example, in one or more embodiments, one or more portions of the housing 14 can be hermetically sealed together utilizing one or more laser diffusion bonding techniques described in co-owned U.S. Pat. No. 10,124,559 B2, entitled KINETICALLY LIMITED NANO-SCALE DIFFUSION BOND STRUCTURES AND METHODS.

The IMD 12 include the electrodes 18, 20 that can be connected to the housing utilizing any suitable technique or techniques. In one or more embodiment, at least one of the electrodes 18, 20 can be mechanically connected to housing 14. In one or more embodiments, at least one of the electrodes 18, 20 can be defined by an outer portion of the housing 14 that is electrically conductive. For example, electrode 20 can be defined by a tissue-exposed conductive portion of housing 14.

Electrodes 18, 20 are electrically isolated from each other. Electrode 18 can be referred to as a tip electrode, and fixation tines 16 can be adapted to anchor the IMD 12 to tissue such that electrode 18 maintains contact with the tissue. In one or more embodiments, fixation tines 16 can also be electrically connected to one or more electronic components such that the tines are adapted to direct an electrical signal to tissue of the patient and/or receive an electronic signal from the tissue. In one or more embodiments, a portion of housing 14 can be covered by, or formed from, an insulative material to isolate electrodes 18 and 20 from each other and/or to provide a desired size and shape for one or both of electrodes.

Electrode 20 can be a portion of housing 14, e.g., second portion 24, that does not include such insulative material. Electrode 20 can be most or all of housing 14, but most of the housing (other than electrode 20) can be covered with an insulative coating. In one or more embodiments, electrode 20 may be coated with materials to promote conduction. In one or more embodiments, electrode 20 can be part of a separate ring portion of housing 14 that is conductive. Electrodes 18, 20, which may include conductive portion(s) of the first portion 22 of housing 14, can be electrically connected to at least some electronics of pacing device 12 (e.g., sensing circuitry, electrical stimulation circuitry, or both). In one or more embodiments, the housing 14 can include an end cap 26 that can house or enclose a feedthrough header assembly (e.g., feedthrough header assembly 42 of FIG. 3) to electrically connect the electrode 18 to the electronics within the housing 14 while electrically isolating the electrode from the housing 14, e.g., including electrode 20 or other conductive portions of the housing.

In the embodiment illustrated in FIG. 2, the housing 14 includes the first portion 22 and the second portion 24. The first portion 22 can be disposed adjacent to the first end 6 of the housing 14, and the second portion 24 can be disposed adjacent to the second end 8 of the housing. As used herein, the term "adjacent to the first end" means that an element or component is disposed closer to the first end 6 of the housing 14 than to the second end 8 of the housing. Further, the term "adjacent to the second end" means that an element or component is disposed closer to the second end 8 of the housing 14 than to the first end 6 of the housing. The second portion 24 can, in one or more embodiments, define at least part of a power source case that houses a power source (e.g., a battery) of the IMD 12. In one or more embodiments, the second portion 24 can include the conductive portion of the housing 14 that forms the electrode 20.

The first portion 22 of the housing 14 can be connected to the second portion 24 of the housing using any suitable technique or techniques. In one or more embodiments, the first portion 22 of the housing 14 can be connected to the second portion 24 of the housing using laser bonding. For example, electromagnetic radiation (e.g., light) can be directed through an outer surface of the first portion 22 and focused at an interface between the first portion and the second portion 24 to form a laser bond.

Any suitable electromagnetic radiation can be utilized to form a bond between the first portion 22 and the second portion 24 of the housing 14. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 10,000 nm. For example, laser light can include UV light, visible light, IR light, and combinations thereof. In one or more embodiments, a UV laser can be utilized to provide light having a wavelength of about 350 nm and a pulse width of about 30 ns. In one or more embodiments, the materials for the first and second portions 22, 24 of the housing 14, and the power level and wavelength of the light used may be selected such that the light may not directly damage, ablate, warp, or cut the housing, and such that the first and second portions of the housing retain their bulk properties.

In general, light can be provided by any suitable laser or laser system. For example, the laser may generate light having a relatively narrow set of wavelengths (e.g., a single wavelength). The light emitted by the laser may form a collimated beam that may not be focused at a particular point. The light emitted by the laser may be focused at interfaces between the first portion 22 and the second portion 24 of the housing 14 to generate a laser bond.

Although the laser may provide light that has a narrow range of wavelengths, in one or more embodiments, the laser may represent one or more devices that emit light having a wider range of wavelengths than a single typical laser. A wide variety of devices may be used to emit light having a narrow or wide range of wavelengths. In one or more embodiments, the laser may include one or more laser devices including diode and fiber lasers. Laser sources may also include, e.g., TI sapphire, argon ion, Nd:YAG, XeF, HeNe, Dye, GaAs/AlGaAs, $CO_2$, Alexandrite, InGaAs, InGaAsP, Nd:glass, Yb:YAG, or Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 µm, with a top hat or Gaussian spatial energy profile.

In the embodiment of FIG. 2, the IMD 12 can also include a flange 28 connected to the second portion 24 of the housing 14 at the second end 8 of the housing that defines an opening. The flange 28 can enable medical instruments to attach to the IMD 12, e.g., for delivery and/or extraction of the device. For example, a tether that extends through a catheter inserted into the heart 4 (FIG. 1) can be attached to the flange 28 and/or threaded through the opening to implant or extract the IMD 12.

Figure 3:
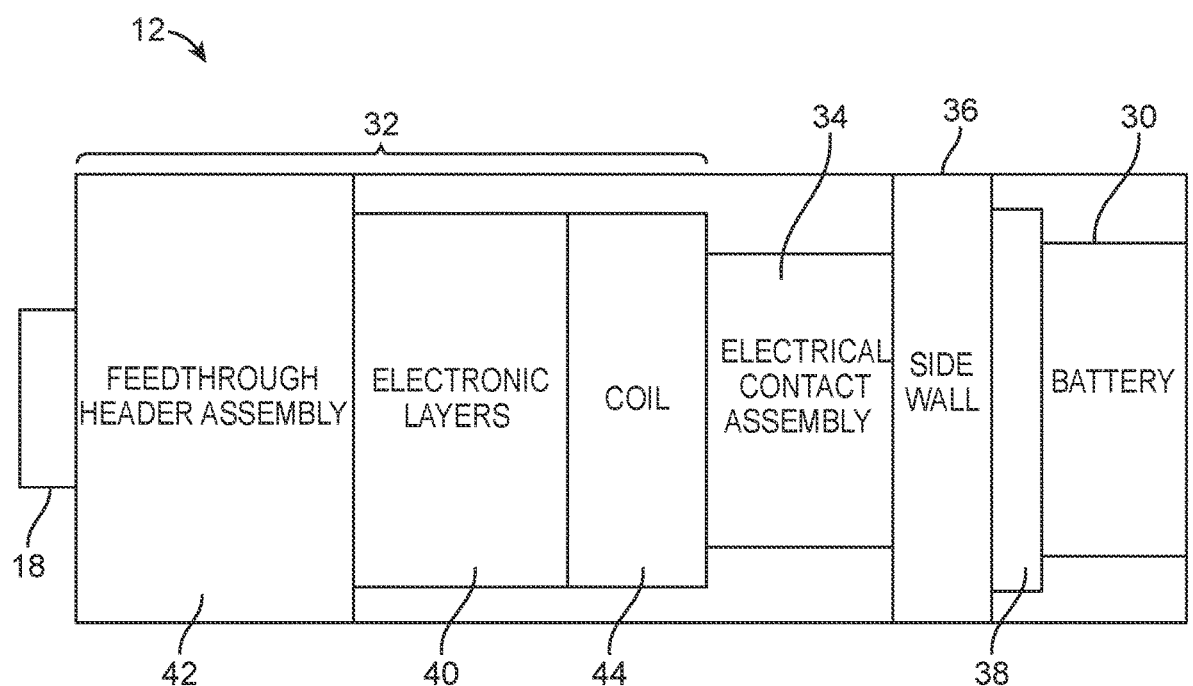
FIG. 3 is a schematic block diagram view of the implantable medical device of FIG. 1.

FIG. 3 is a schematic block diagram of one embodiment of the IMD 12 including a power source 30 (e.g., battery), an electronics module 32, and an electrical contact assembly 34. Although the IMD of FIG. 3 is described as IMD 12, the structures shown in FIG. 3 can also be used in other implantable or external medical devices, such as cardioverter-defibrillators, physiological monitors, or neurostimulators, or any other electronic devices.

The housing 14 includes the first and second portions 22, 24 and a side wall 36 disposed within the housing between the battery 30 and the electrical contact assembly 34. The side wall 36 can be disposed within the first and second housing portions 22, 24 or at the boundary of first and second housing portions. In one or more embodiments, the first and second housing portions 22, 24 are common with a ground terminal of battery 30. In one or more embodiments, one or both of the first and second housing portions 22, 24 is non-conductive. For example, first housing portion 22 can be formed of a non-conductive material, such as sapphire, which may allow easier transmission of electromagnetic signals into and out of the housing 14 than a metal or other conductive material would allow.

As shown in the embodiment illustrated in FIG. 3, the side wall 36 extends across housing 14 between the battery 30 on one side and electrical contact assembly 34 on the other side. The side wall 36 can include at least one feedthrough (not shown) to allow for electrical connection between the battery 30 and the electronics module 32. As discussed herein, feedthrough header assembly 42 can also include at least one feedthrough to allow for an electrical connection between electrode 18 and electronic layers 40. Electronics module 32 is disposed between the electrode 18 and electrical contact assembly 34. In one or more embodiments, electrical contact assembly 34 can be fixed to side wall 36 to provide mechanical support for the electronics module 32. The electronic contact assembly 34 provides an electrical connection between the battery 30 and the electronics module 32.

The IMD 12 can also include a battery header 38 disposed between the battery 30 and the electrical contact assembly 34. The side wall 36 can form part or all of the battery header 38. The battery header 38, the side wall 36, and the electrical contact assembly 34 can be electrically connected to the electronics module 32 using any suitable technique or techniques. In one or more embodiments, the battery header 38, the side wall 36, and/or electrical contact assembly 34 can include feedthroughs and/or openings for creating an electrical connection between the battery 30 and electronics module 32.

The electrical contact assembly 34 can include any suitable assembly for electrically connecting the electronics module 32 and the battery 30, e.g., one or more embodiments of electrical contact assemblies described in co-owned U.S. patent application Ser. No. 17/071,463, entitled ELECTRONICS ASSEMBLY FOR IMPLANTABLE MEDICAL DEVICE. In one or more embodiments, the electrical contact assembly 34 can include a spring contact for holding electronics module 32 in place and for providing electrical connections between the electronics module and the battery 30.

The IMD 12 can be manufactured utilizing a single tube for the first housing portion 22 or as two tube sections for such housing portion. Using a single tube for the housing portion 22, in contrast to two sections, e.g., two half-pipes, may lower the cost and complexity of the encasement for pacing device 12. A single tube opens up new encasement options and can be manufactured from alternate materials. For example, a single sapphire tube utilized for the first housing portion 22 can allow for wireless charging of the battery 30 even when the IMD 12 is implanted within a patient.

In one or more embodiments, at least one of the first and second portions 22, 24 of the housing 14 can include a substantially transparent material. As used herein, the phrase "substantially transparent" means that the portion 22, 24 of the housing 14 transmits greater than 50% of electromagnetic radiation incident on the portion for a selected wavelength or range of wavelengths, assuming no reflection at the air-substrate boundaries. In one or more embodiments, at least one of the first and second portions 22, 24 can be substantially transmissive to electromagnetic radiation having a wavelength of at least 200 nm. In one or more embodiments, at least one of the first and second portions 22, 24 can be substantially transmissive to electromagnetic radiation having a wavelength of greater than 10,000 nm. In one or more embodiments, at least one of the first and second portions 22, 24 can be substantially transmissive to electromagnetic radiation having a wavelength in a range of 200 nm to 10,000 nm. In one or more embodiments, at least one of the first and second portions 22, 24 can be substantially transmissive to at least one of UV light, visible light, or IR light. The substantially transparent material can include at least one of glass, quartz, silica, sapphire, silicon carbide, diamond, or gallium nitride.

Figure 4:
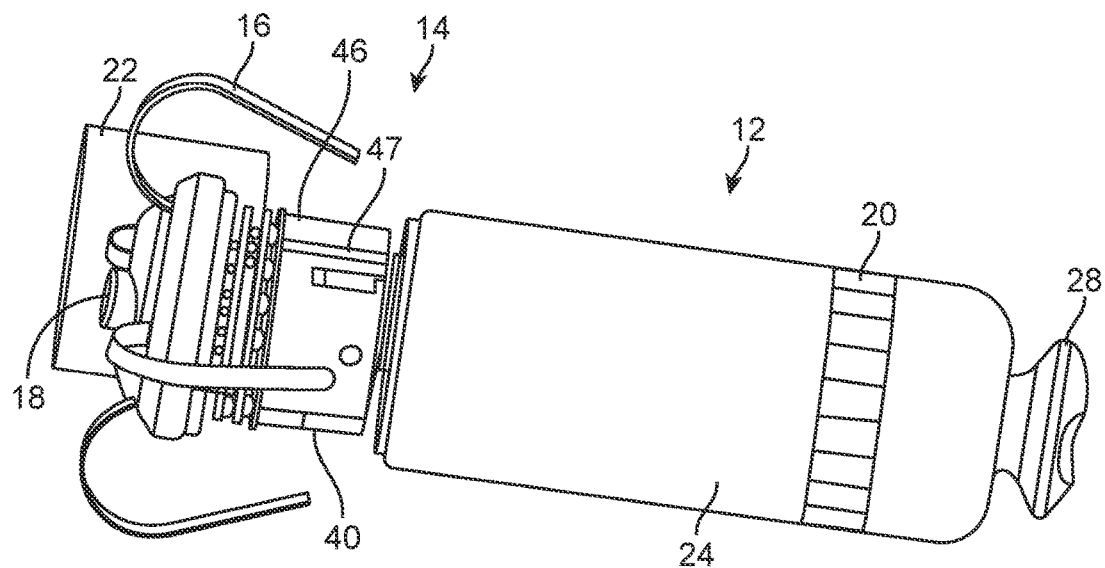
FIG. 4 is a schematic perspective view of the implantable medical device of FIG. 1.

In one or more embodiments, the first housing portion 22 can include a substantially transparent material such that one or more sensors, emitters, or detectors can be disposed within the first housing portion and transmit or receive electromagnetic radiation through such portion. For example, FIG. 4 is a perspective view of the IMD 12 of FIGS. 1-3 with a transparent first portion 22 partially removed for clarity. As shown in FIG. 4, the electronics module 32 is disposed within the first portion 22.

The electronics module 32 can include any suitable elements or components. For example, as shown in FIG. 3, the electronics module 32 includes one or more electronic layers 40 and a feedthrough header assembly 42 electrically connected to the one or more electronic layers 40. The electronics module 32 can also include one or more coils 44 electrically connected to the electronic layers 40.

Figure 5:
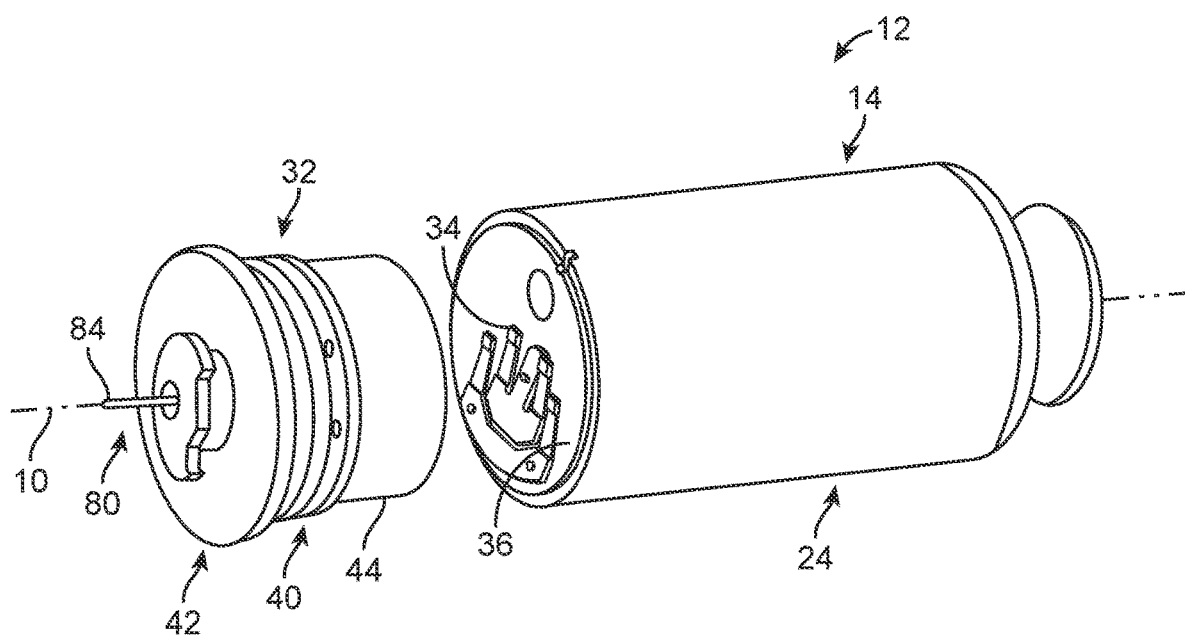
FIG. 5 is a schematic partial exploded view of the implantable medical device of FIG. 1.
Figure 6:
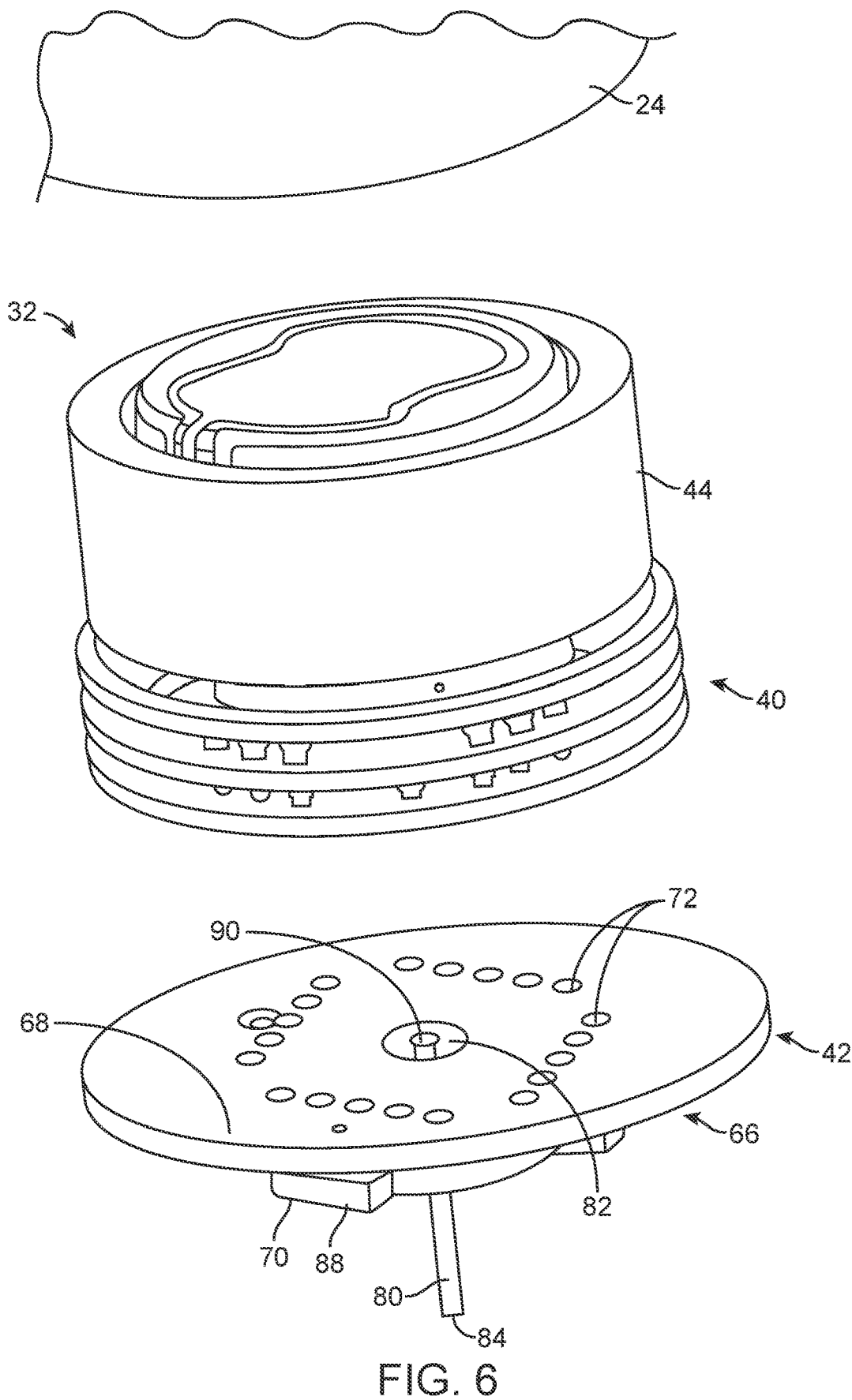
FIG. 6 is a schematic partial exploded view of an electronics module of the implantable medical device of FIG. 1.
Figure 7:
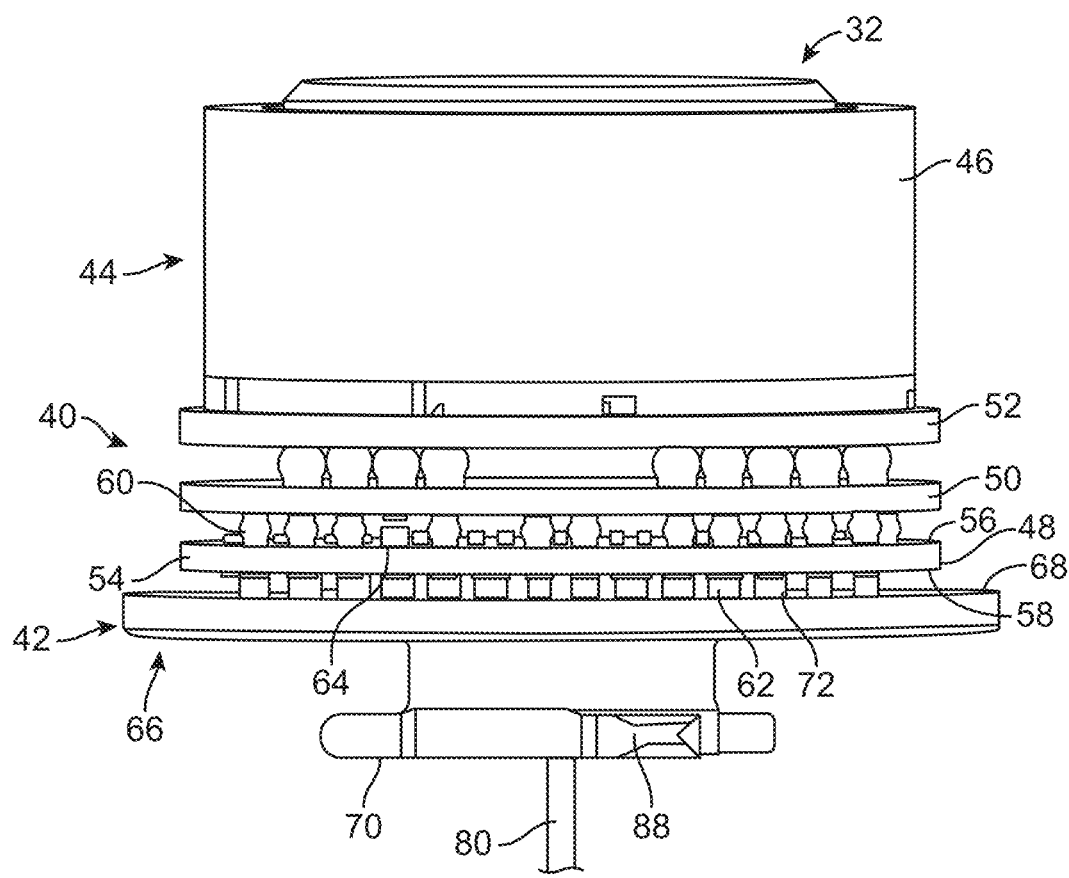
FIG. 7 is a schematic side view of the electronic module of FIG. 6.

FIGS. 5-7 are various schematic views of the electronics module 32 of the pacing device 12 of FIGS. 1-4. The module 32 includes electronic layers 40 and the feedthrough header assembly 42 electrically connected to the electronic layers.

The electronic layers 40 include a first electronic layer 48, a second electronic layer 50, and a third electronic layer 52. Although illustrated as including three electronic layers, the electronic layers 40 can include any suitable number of layers, e.g., one, two, three, four, five, or more layers. Each layer of the electronic layers 40 can include a substrate. For example, first electronic layer 48 includes a substrate 54 having a first major surface 56 and a second major surface 58.

The electronic layers 40 can be disposed in any suitable relationship relative to the feedthrough header assembly 42 and the battery 30. In one or more embodiments, the electronic layers 40 can be disposed such that they are substantially orthogonal to the longitudinal axis 10 (FIG. 5) of the IMD 12, where the housing 14 of the device extends along the longitudinal axis. For example, the first major surface 56 of the substrate 54 of the first electronic layer 48 is substantially orthogonal to the longitudinal axis 10 of the housing 14. As used herein, the term "substantially orthogonal" means that the longitudinal axis 10 forms an angle with a substrate of one or more of the electronic layers 40 of no greater than 10 degrees.

The electronic layers 40 can be electrically connected together using any suitable technique or techniques. In or more embodiments, one or more of the electronic layers 40 can include one or more conductive vias that are disposed through the respective substrate of one or more of the electronic layers. Further, one or more conductive pads 60 can be disposed on one or more of the electronic layers 40 to provide electrical connections between the feedthrough header assembly 42 and the electronic layers, between one or more of the electronic layers, and between the electronic layers and the electrical contact assembly 34. For example, conductive pad 62 is disposed between (e.g., between conductive surfaces of) the feedthrough header assembly 42 and the first electronic layer 48 to provide an electrical connection between the feedthrough header assembly and the first electronic layer. In one or more embodiments, this connection can be between the housing 14 and the first electronic layer 48 or between one or more of the feedthrough pin 80 of the assembly and the first electronic layer. The conductive pads 60 can include any suitable conductive contact, e.g., solder bumps, solder balls, conductive epoxy, braze alloys, etc.

One or more of the electronic layers 40 can include an electronic component disposed on its respective substrate. For example, first electronic layer 48 includes electronic component 64 disposed on the first major surface 56 of the substrate 54. The electronic component 64 can be disposed on at least one of the first major surface 56 or second major surface 58 of the substrate 54. Any suitable number of electronic components can be disposed on one or both major surfaces 56, 58 of the substrate 54. Further, the electronic component 64 can be electrically connected to one or more additional electronic components disposed on the substrate 54 or on the second or third electronic layers 50, 52 using any suitable technique or techniques. In one or more embodiments, the electronic component 64 can be disposed on a patterned conductive layer (not shown) disposed on the substrate 54 using any suitable technique or techniques. One or more conductive vias can be disposed between the first and second major surfaces 56, 58 of the substrate 54 to provide one or more conductive pathways between the patterned conductive layer and other elements or components disposed on an opposite side of the substrate 54 from the electronic component 64. Further, one or more conductive pads 60 can be directly connected to the electronic component 64 to electrically connect the component to one or more additional components or devices.

Electrically connected to one or more of the electronic layers 40 is the coil 44. Such coil 44 can include any suitable number of coils disposed on or within a housing 46 and one or more electronic components also disposed within the housing. The coil 44 can be utilized to inductively couple the IMD 12 with an external inductive charging system for charging the device when it is implanted within the body of the patient 4 or for telemetry or other types of communication with a transceiver that is external to the patient's body. The coil 44 can be electrically connected to the electronic layers 40 using any suitable technique or techniques. Further, the coil 44 can be electrically connected, e.g., to third electronic layer 52 using any suitable technique or techniques. The housing 46 of the coil 44 can provide one or more electrical pathways between the battery 30 and the electronic layers 40 using any suitable technique or techniques. In one or more embodiments, one or more conductors 47 (FIG. 4) can be disposed on or within the housing 46 to provide one or more of these electrical pathways.

Also electrically connected to one or more of the electronic layers 40 is the feedthrough header assembly 42. As shown in FIGS. 5-8, the assembly 42 includes a conductive header 66 that has an inner surface 68, an outer surface 70, and one or more contacts 72 disposed on the inner surface and electrically connected to the header. The assembly 42 further includes a feedthrough pin 80 disposed within a via 86 (FIG. 8) that extends through the header 66 between the inner surface 68 and the outer surface 70 of the header. The feedthrough pin 80 is electrically isolated from the header 66 and includes a first end 82 adjacent to the inner surface 68 of the header and a second end 84 adjacent to the outer surface 70 of the header. As used herein, the term "adjacent to the inner surface" means that an element or component is disposed closer to the inner surface 68 of the header 66 than to the outer surface 70 of the header. Further, as is also used herein, the term "adjacent to the outer surface" means that an element or component is disposed closer to the outer surface 70 of the header 66 than to the inner surface 68.

The assembly 42 can take any suitable shape or shapes and have any suitable dimensions. In one or more embodiments, the assembly 42 can include an elliptical cross-section in a plane substantially parallel to the inner surface 68 of the header 66.

The header 66 can also take any suitable shape or shape and have any suitable dimensions. Further, the header 66 can include any suitable material or materials, e.g., at least one of titanium, copper, niobium, tantalum, or alloys thereof. In one or more embodiments, the header 66 is electrically conductive.

The header 66 can include a flange 88 that at least in part forms the outer surface 70 of the header. The flange 88 can be adapted to connect the header 66 to the end cap 26 (FIG. 2).

The feedthrough header assembly 42 can further include one or more conductive contacts 72 disposed on the inner surface 68 of the header 66 and electrically connected to the header. Any suitable number of contacts 72 can be disposed on the inner surface 68 in any suitable arrangement or array. The contacts 72 can include any suitable conductive structure, e.g., at least one of a solder bump, solder paste, conductive epoxy, or conductive joint.

Figure 8:
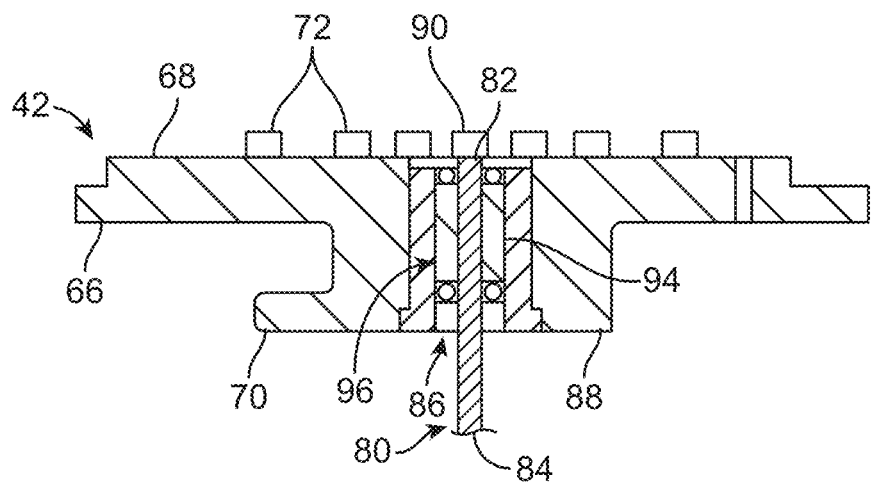
FIG. 8 is a schematic cross-section view of a feedthrough header assembly of the electronics module of FIG. 6.
Figure 9:
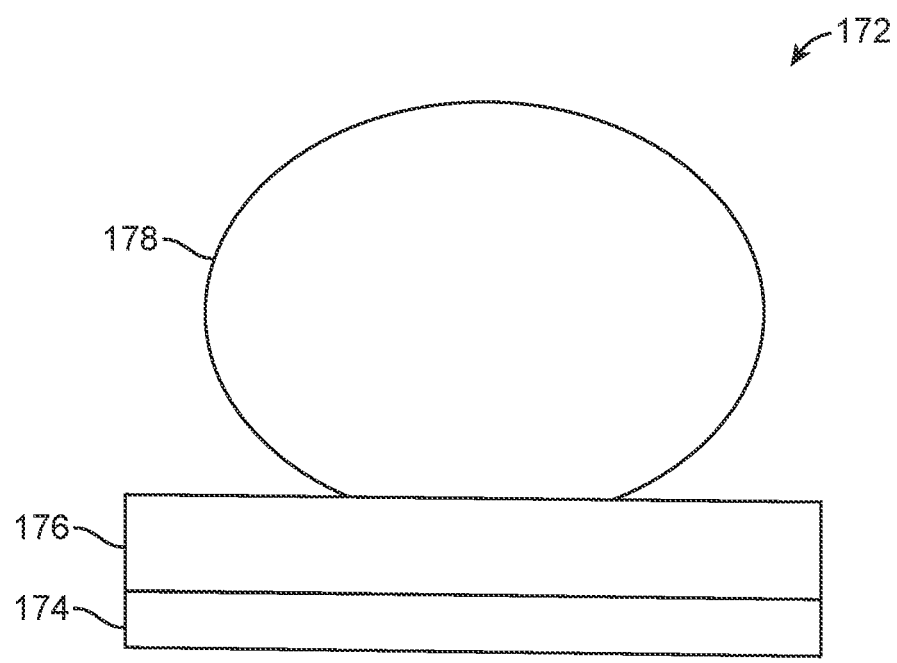
FIG. 9 is a schematic cross-section of one embodiment of a contact of a feedthrough header assembly.

For example, FIG. 9 is a schematic cross-section view of one embodiment of a contact 172. The contact 172 can include a seed or adhesion layer 174 disposed on an inner surface of a conductive header (e.g., inner surface 68 of conductive header 66 of FIGS. 5-8), a conductive layer 176 disposed on the seed layer, and a solder ball 178 disposed on the conductive layer such that the conductive layer and the seed layer are between the solder ball and the conductive inner surface of the header. The seed layer 174 and the conductive layer 176 can include any suitable conductive material or materials, e.g., a material that improves adhesion of subsequent metal layers such as nickel, nickel-vanadium, titanium, zirconium, etc. The conductive layer 176 can be additional metallization to provide enhanced conduction and solderability such as copper, gold, tin-lead, or other solderable conductive materials. The seed layer 174 and conductive layer 176 can include the same materials or different materials. Further, the seed layer 174 and the conductive layer 176 can be disposed using any suitable technique or techniques, e.g., plating, sputtering, sintering, vapor deposition, etc. In one or more embodiments, the seed layer 174 can be disposed on the inner surface of the header followed by deposition of the conductive layer 176 on the seed layer. The seed and conductive layers 174, 176 can be patterned using any suitable technique or techniques to form contacts. The solder ball 178 can also include any suitable conductive material or materials, e.g., the same materials described herein regarding contacts 72, can be disposed on the conductive layer using any suitable technique or techniques, e.g., physical masking of non-target areas during vapor deposition or plating, laser defined patterns by removal of undesired material after full deposition, etc.

Returning to FIGS. 5-8, the contacts 72 can be disposed on the inner surface 68 of the header 66 using any suitable technique or techniques, e.g., sputtering, plating, etc. For example, a conductive material can be disposed on the inner surface 68 and then patterned to form the contacts 72. In one or more embodiments, the contacts 72 can be integral with the header 66, i.e., the contacts and the header are formed as a single entity.

The contacts 72 can be adapted to electrically connect the header 66 to one or more of the electronic layers 40 of the electronics module 32. In one or more embodiments, the contacts 72 can provide redundant connections between the header 66 and other components of the IMD 12, e.g., one or more of the electronic layers 40. The electronic components 64 of the electronic layers 40 can be electrically connected to the one or more contacts 72 of the conductive header 66 such that the electronic components are electrically connected to the header 66. In one or more embodiments, the major surface of the substrate of an electronic layer of the layers 40 faces the conductive inner surface 68 of the header 66 without any intervening nonconductive layers disposed between the major surface of the substrate and the conductive inner surface 68 of the header 66. For example, as shown in FIG. 7, the second major surface 58 of the substrate 54 of the first electronic layer 48 faces the conductive inner surface 68 of the header 66 without any intervening nonconductive layers disposed between the second major surface of the substrate and the conductive inner surface of the header. Conductive pads 60 of the first electronic layer 48 that are disposed on the second major surface 58 of the substrate 54 are spaced apart from the conductive inner surface 68 of the header 66 and isolated from the header by a gap that is formed between the electronic layers 40 and the header. No nonconductive layers are, therefore, required between the electronic layers 40 and the header 66 to isolate the electronic layers from the header.

Disposed through the header 66 between the inner surface 68 and the outer surface 70 is the via 86. The via 86 can take any suitable shape or shapes and have any suitable dimensions. In one or more embodiments, the via 86 can have a cross-sectional area in a plane parallel to the inner surface 68 of the header 66 that is greater than a cross-sectional area of the feedthrough pin 80 in the same plane.

The feedthrough pin 80 is disposed within the via 86 of the header 66 and includes the first end 82 that is adjacent to the inner surface 68 of the header 66 and the second end 84 that is adjacent to the outer surface 70 of the header. The feedthrough pin 80 can include any suitable material or materials, e.g., the same materials described herein regarding the header 66. Further, the feedthrough pin 80 can take any suitable shape or shapes and have any suitable dimensions. In one or more embodiments, the first end 82 of the feedthrough pin 80 can extend beyond the inner surface 68 of the header 66 any suitable length. In one or more embodiments, the first end 82 of the feedthrough pin 80 can be flush with the inner surface 68 of the header 66 such that an end surface at the first end of the feedthrough pin 80 is in a plane defined by the inner surface 68 of the header 66, or the first end can be recessed from the inner surface such that the first end is disposed within the via 86.

As mentioned herein, the feedthrough pin 80 can be electrically isolated from the header 66 using any suitable technique or techniques. For example, insulating material 94 can be disposed within the via 86. As shown in FIG. 8, insulating material 94 can be disposed within the via 86 between a wall portion 96 of the via and the feedthrough pin 80 and at least a portion 96 of the via 86 such that the feedthrough pin is electrically isolated from the header. Any suitable insulating material 94 can be utilized to isolate the feedthrough pin 80 within the via 86, e.g., glass, sapphire, epoxy, or other non-conductive material that provides a seal, etc.

The feedthrough pin 80 can be adapted to be electrically connected to one or more of the electronic layers 40 of the electronics module 32. In one or more embodiments, the feedthrough pin 80 can include a contact 90 disposed at the first end 82 of the pin. The contact 90 can include any suitable contact or contacts, e.g., contact 72. The contact 90 can be disposed at the first end 82 of the pin 80 using any suitable technique or techniques. In one or more embodiments, the contact 90 is integral with the first end 82 of the pin 80 and can take any suitable shape or shapes, e.g., the pin and contact can form a nail head at the first end of the pin. Further, in one or more embodiments, a conductive pad or pads can be electrically connected to the feedthrough pin 80 to provide an electrical connection between the feedthrough pin and one or more of the electronic layers 40.

Figure 10:
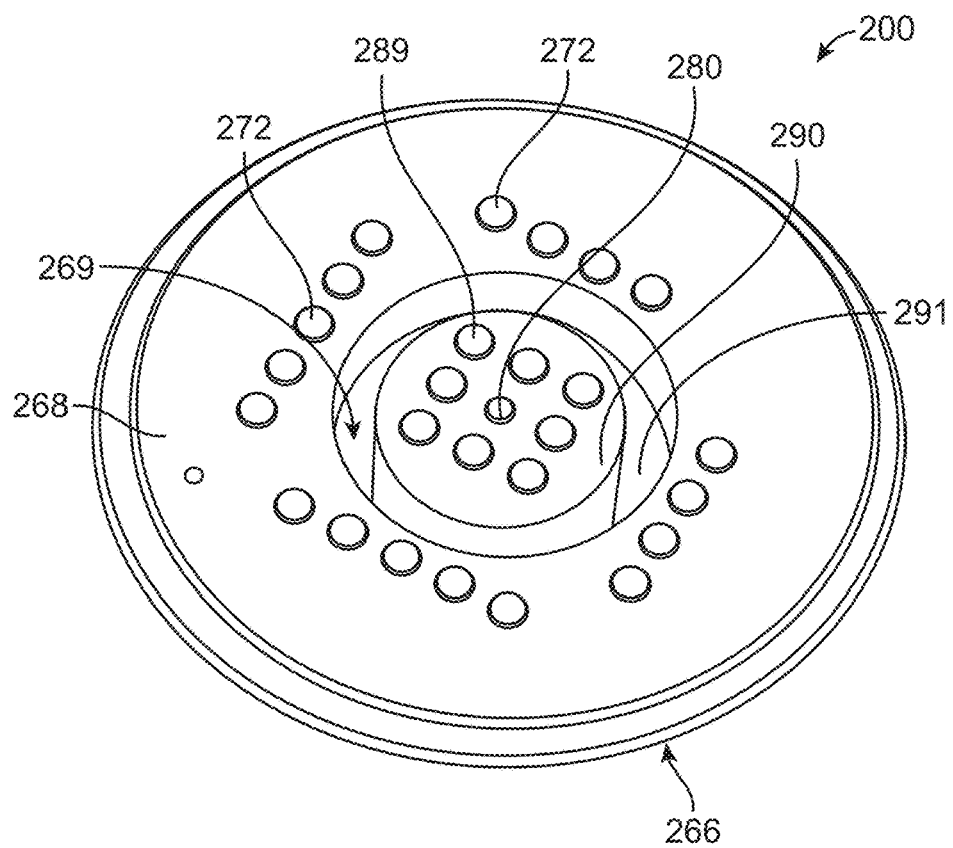
FIG. 10 is a schematic perspective view of another embodiment of a feedthrough header assembly.
Figure 11:
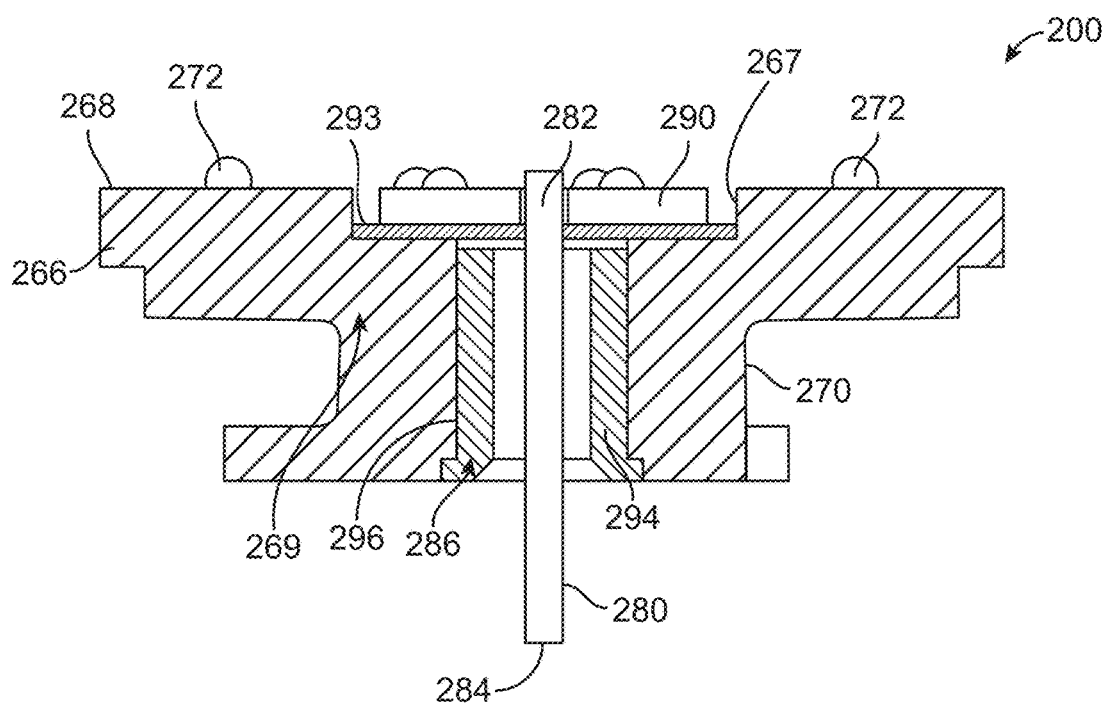
FIG. 11 is a schematic cross-section view of the feedthrough header assembly of FIG. 10.

For example, FIGS. 10-11 are schematic perspective and cross-section views of another embodiment of a feedthrough header assembly 200. All of the design considerations and possibilities described herein regarding feedthrough header assembly 42 of FIGS. 5-8 apply equally to feedthrough header assembly 200 of FIGS. 10-11. The assembly 200 includes a header 266 that has a conductive inner surface 268, an outer surface 270, and one or more contacts 272 disposed on the inner surface and electrically connected to the header. The assembly further includes a feedthrough pin 280 disposed within a via 286 that extends through the header to 266 between the inner surface 268 and the outer surface 270 of the header. The feedthrough pin 280 is electrically isolated from the header 266 and includes a first end 282 adjacent to the inner surface 268 of the header 266 and a second end 284 adjacent to the outer surface 270 of the header.

One difference between the feedthrough header assembly 200 of FIGS. 10-11 and the assembly 42 of FIGS. 5-8 is that the assembly 200 includes a conductive pad 290 disposed at the first end 282 of the feedthrough pin 280. The conductive pad 290 is electrically connected to the feedthrough pin 280 using any suitable technique or techniques, e.g., the conductive pad can be welded to the feedthrough pin. In one or more embodiments, the conductive pad 290 is integral with the feedthrough pin 280. The conductive pad 290 can take any suitable shape or shapes and have any suitable dimensions. In one or more embodiments, one or more contacts 289 can be disposed on the conductive pad 290 that are electrically connected to the conductive pad using any suitable technique or techniques. The conductive pad 290 can electrically connect the feedthrough pin 280 and one or more electronic layers of an electronic module (e.g., electronic layers 40 of electronic module 32 of FIGS. 3-7). Further, the conductive pad can include any suitable conductive material or materials, e.g., at least one of copper, niobium, titanium, platinum, or platinum-iridium.

In one or more embodiments, the conductive pad 290 can be disposed within a recessed surface 269 disposed in the inner surface 268 of the header 266. The recessed surface 269 can take any suitable shape or shapes and have any suitable dimensions. In one or more embodiments, the recessed surface 269 can have a depth that is substantially equal to a thickness of the conductive pad 290 such that the pad is substantially flush with the inner surface 268 of the header 266. The conductive pad 290 can be electrically isolated from the header 266 using any suitable technique or techniques. In one or more embodiments, the conductive pad 290 is electrically isolated from the header 266 by a nonconductive layer 291 disposed between the conductive pad 290 on the recessed surface 269. The nonconductive layer 291 can include any suitable nonconductive material or materials. In one or more embodiments, the nonconductive layer 291 is a ceramic disk disposed within the recessed surface 269 of the inner surface 268 of the header 266. Further, in one or more embodiments, insulative material 293 can be disposed between the conductive pad 290 and one or more side portions 267 of the recessed surface. The insulative material 293 can include any suitable material or materials, e.g., at least one of glass, sapphire, ceramic, or epoxy or other insulative polymer. In one or more embodiments, the insulative material 293 and the nonconductive layer 291 can be the same material or materials. In one or more embodiments, the insulative material 293 and the nonconductive layer 291 are integral.

The assembly 200 also includes a housing 294 disposed within the via 286 between a wall portion 296 of the via and the feedthrough pin 280. The housing 294 can include any suitable material or materials. Insulative material 293 can also be disposed between the feedthrough pin 280 and the housing 294.

Figure 12:
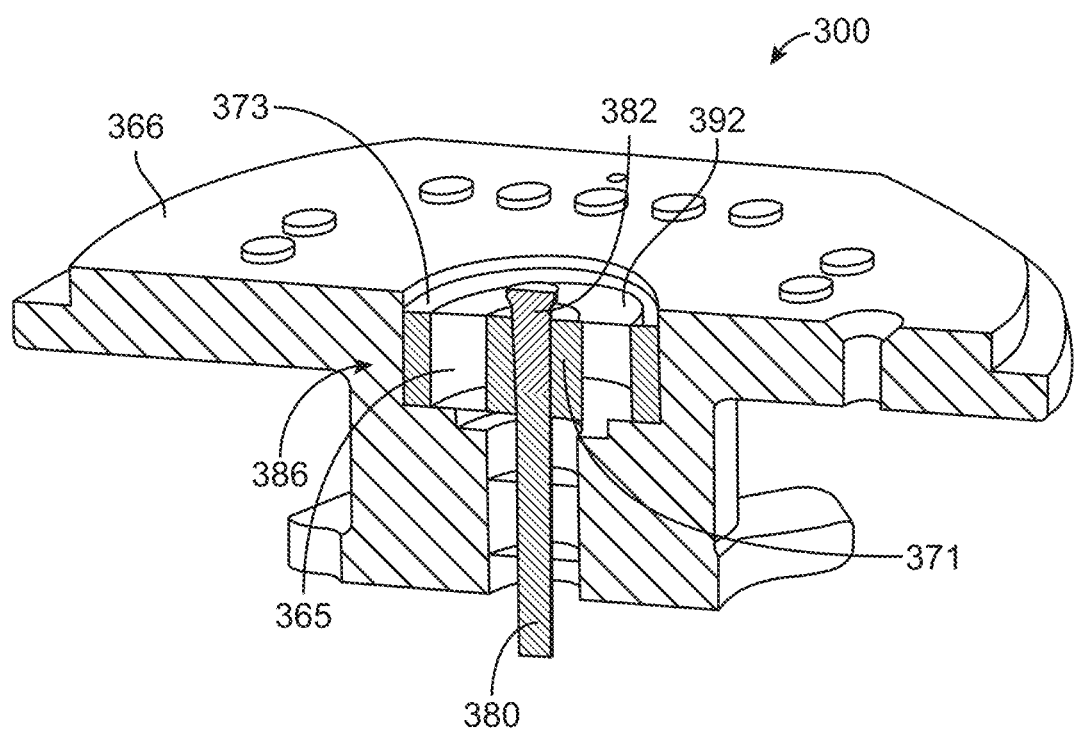
FIG. 12 is a schematic perspective cross-section view of another embodiment of a feedthrough header assembly.

The various feedthrough header assemblies described herein can further include one or more electronic devices. For example, FIG. 12 is a schematic perspective view of another embodiment of a feedthrough header assembly 300. All of the design considerations and possibilities described herein regarding feedthrough header assemblies 12 and 200 apply equally to feedthrough header assembly 300. One difference between assembly 300 and assemblies 12 and 200 is that assembly 300 includes a header electronic device 392 disposed at a first end 382 of feedthrough pin 380. The header electronic device 392 is electrically connected to feedthrough pin 380 using any suitable technique or techniques. Further, the header electronic device 392 can include any suitable electronic device or devices, e.g., at least one of a capacitor, inductor, or other electrically filtering components. In one or more embodiments, the header electronic device is electrically isolated from header 366 using any suitable technique or techniques.

Another difference between assembly 300 and assemblies 12 and 200 is that a capacitor 365 is disposed within via 386 of the header 366. The capacitor 365 can include any suitable capacitor and can be electrically connected to the pin 380 and the header 366 using any suitable technique or techniques. In one or more embodiments, an inner surface 371 of the capacitor 365 can be electrically connected to the pin 380, and an outer surface 373 of the capacitor can be electrically connected to the header 366.

Figure 16:
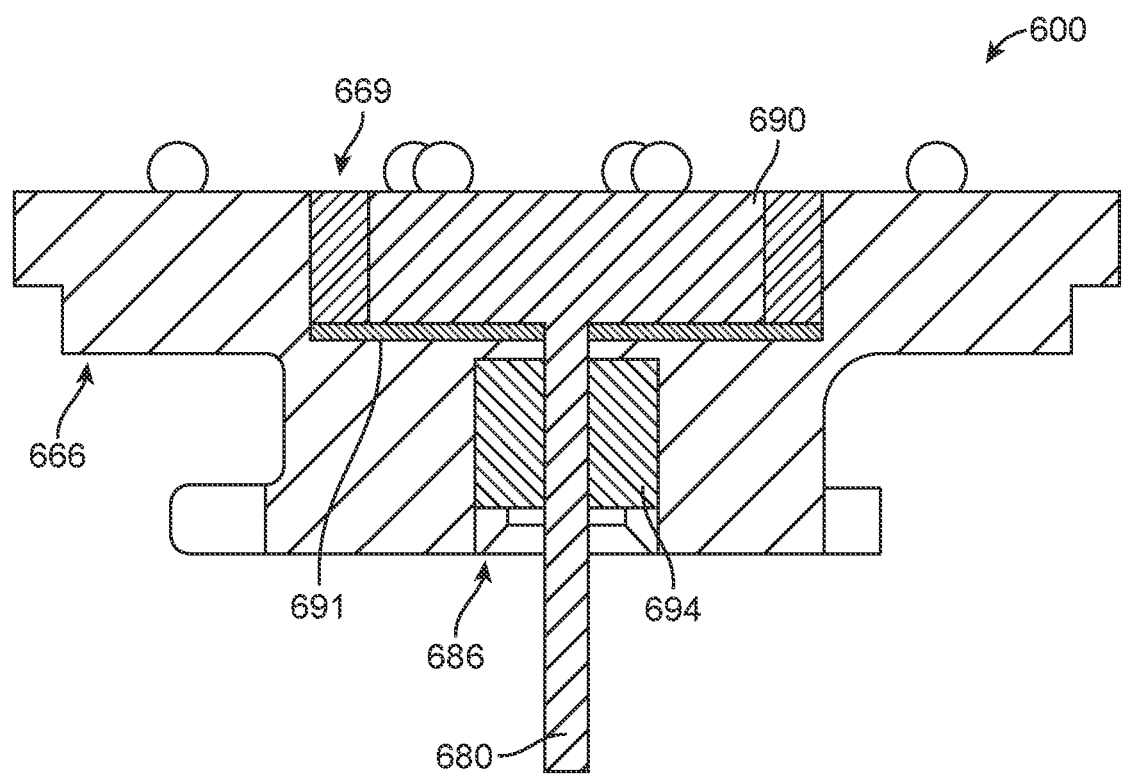
FIG. 16 is a schematic cross-section view of another embodiment of a feedthrough header assembly.

FIG. 16 is a schematic cross-section view of another embodiment of a feedthrough header assembly 600. All of the design considerations and possibilities described herein regarding feedthrough header assemblies 12, 100, 200, and 300 apply equally to feedthrough header assembly 600. One difference between assembly 600 and assemblies 12, 100, 200, and 300 is that feedthrough pin 680 and contact 690 are integral. An insulating layer or disk 691 can be disposed between the contact 690 and a recessed surface 669 of header 666 to electrically isolate the contact 690 from the header. In one or more embodiments, disk 691 can be a ceramic disk. Further, an insulative material 694 such as glass can be disposed between one or more portions of the feedthrough pin 680 and via 686 to electrically isolate the feedthrough pin from the header 666. In one or more embodiments, insulative material 694 can instead be disposed between the recessed sidewalls of the recessed surface 669 and the contact 690.

Figure 13:
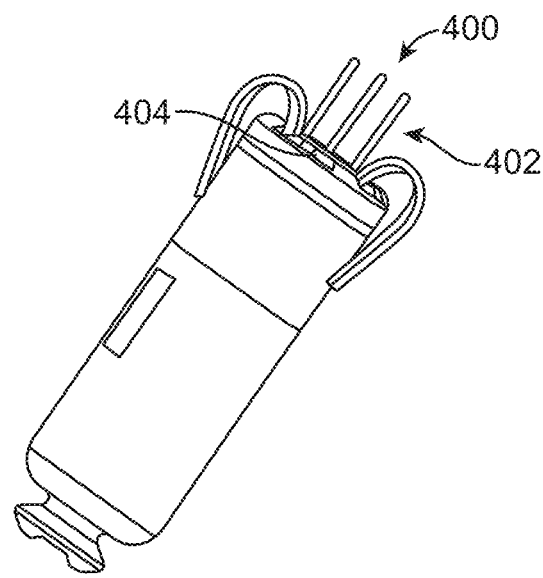
FIG. 13 is a schematic perspective view of another embodiment of an implantable medical device.
Figure 14:
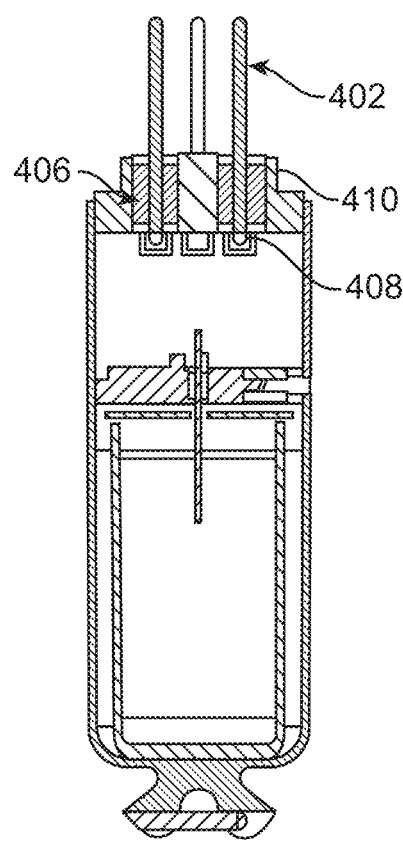
FIG. 14 is a schematic cross-section view of the implantable medical device of FIG. 13.

The various embodiments of feedthrough header assemblies described herein can include any suitable number of feedthrough pins, e.g., two, three, four, five, or more feedthrough pins. For example, FIGS. 13-14 are various views of another embodiment of a pacing device 400. All of the design considerations and possibilities described herein regarding implantable medical device 12 of FIGS. 1-8 apply equally to the implantable medical device 400 of FIGS. 13-14.

One difference between device 400 and device 10 is that device 400 includes four feedthrough pins 402 that extend from an endcap 404 of the device. Each of the feedthrough pins 402 can be electrically connected to an electronic layer or layers of an electronics module (e.g., one or more electronic layers 40 of electronics module 32 of FIG. 7). For example, each of the feedthrough pins 402 can have a solder joint 408 that connects the pin to an electronic layer. Further, each of the feedthrough pins 402 can be disposed within a via 406 that extends through header 410. In one or more embodiments, two or more of the feedthrough pins 402 can be disposed in the same via 406 and electrically isolated using an insulating material. In one or more embodiments, each feedthrough pin 402 can be disposed in its own respective via 406. Further, each of the feedthrough pins 402 can extend beyond an outer surface of the header 410 as shown in FIG. 8 regarding feedthrough pin 80 and header 66.

Figure 15:
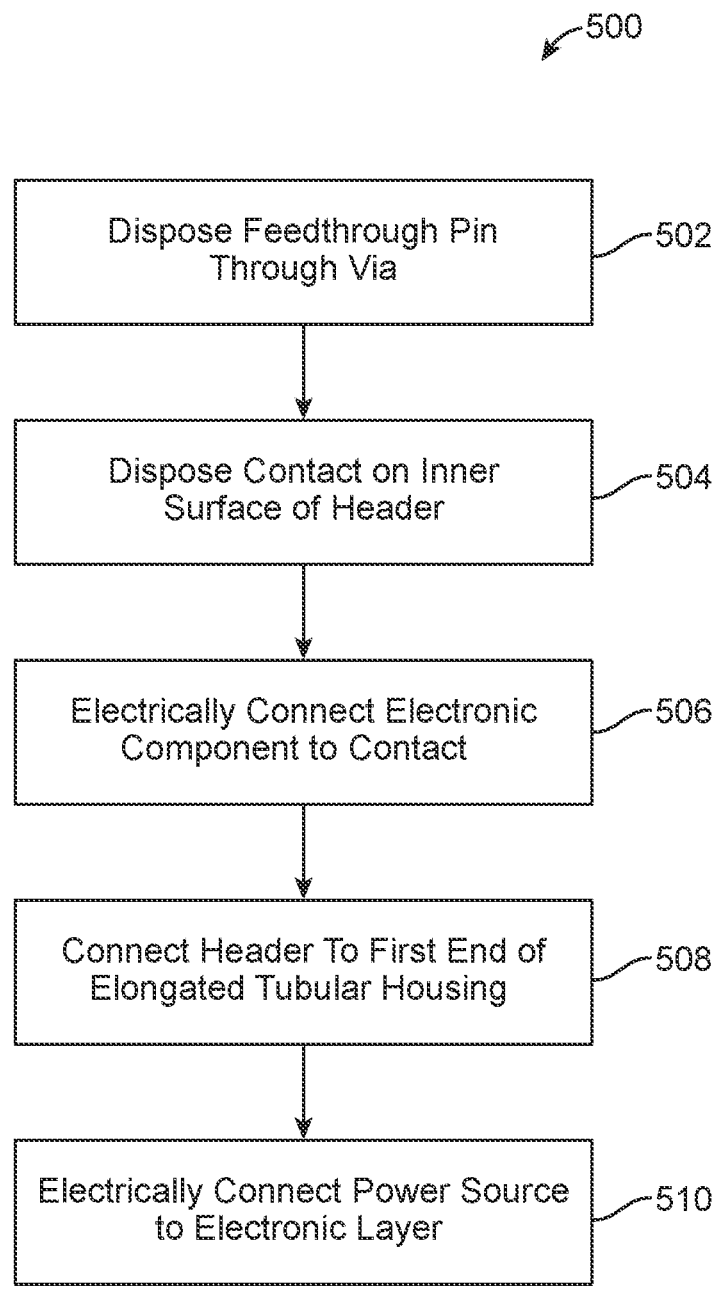
FIG. 15 is a flowchart of one embodiment of a method of forming an implantable medical device.

The various embodiments of pacing devices, electronic modules, and feedthrough header assemblies described herein can be manufactured utilizing any suitable technique or techniques. For example, FIG. 15 is a flowchart of one embodiment of a method 500 for forming the pacing device 12. Although described regarding pacing device 12 of FIGS. 1-8, the method can be utilized to form any suitable implantable medical device.

At 502, the feedthrough pin 80 can be disposed through the via 86 of the conductive header 66 using any suitable technique or techniques. In one or more embodiments, a portion of the feedthrough pin 80 adjacent to the inner surface 68 of the conductive header 66 can be removed such that an end surface at the first end 82 of the feedthrough pin is in a plane defined by the inner surface 68 of the conductive header. Any suitable technique or techniques can be utilized to remove the portion of the feedthrough pin 80, e.g., the first end 82 can be planarized. In one or more embodiments, the inner surface 68 can also be planarized along with the first end 82 of the feedthrough pin 80.

At 504, one or more contacts 72 can be disposed on the inner surface 68 of the header 66 such that it is electrically connected to the header. Any suitable technique or techniques can be utilized to dispose the one or more contacts 72 on the inner surface 68. In one or more embodiments, a seed layer (e.g., seed layer 174 of FIG. 9) can be disposed on the conductive inner surface 68 of the conductive header 66, and a conductive layer (e.g., conductive layer 176 of FIG. 9) can be disposed on the seed layer (e.g., by sputtering), the seed layer and conductive layer can be patterned using any suitable technique or techniques, and a solder ball or contact pad (e.g., solder ball 178 of FIG. 9) can be disposed on the patterned conductive layer. In one or more embodiments, the seed layer can be patterned prior to deposition of the conductive layer. In one or more embodiments, the seed layer and conductive layer can be patterned together.

At 506 one or more electronic components 64 of one or more electronic layers 40 can be electrically connected to the contact 72 such that the electronic component is electrically connected to the header 66. The major surface 56 of the substrate 54 of the electronic layer 48 (i.e., the second major surface) faces the conductive inner surface 68 of the header 66 without any intervening nonconductive layers disposed between the major surface of the substrate and the conductive inner surface of the header. The feedthrough pin 80 can also be electrically connected to one or more electronic layers 40 using any suitable technique or techniques.

At 508, the header 66 can be connected to the first end 6 of the elongated tubular housing 14 such that the electronics module 32 (e.g., one or more electronic layers 40) is disposed within the housing. Any suitable technique or techniques can be utilized to connect the header 66 to the first end 6 of the housing 14. In one or more embodiments, the endcap 26 is connected to the header 66, where the end cap defines the first end 6 of the housing 14.

At 510, a power source (e.g., battery 30) can be electrically connected to one or more of the electronic layers 40, e.g., by pressing a first side of the electronics module 32 against the electrical contact assembly 34. The first portion 22 of the housing 14 can be disposed over the electronics module 32 and connected to the second portion 24 of the housing 14 using any suitable technique or techniques, e.g., laser bonding. Further, the end cap 26 can be connected to the header 66 of the feedthrough assembly 42 of the electronics module 32 using any suitable technique or techniques, e.g., welding.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electronics module comprising:
a feedthrough header assembly comprising:
a conductive header comprising a conductive inner surface, an outer surface, and a contact disposed on the inner surface and electrically connected to the conductive header; and
a feedthrough pin disposed within a via that extends through the conductive header between the inner surface and the outer surface of the conductor header, wherein the feedthrough pin is electrically isolated from the conductive header and comprises a first end adjacent to the inner surface of the conductive header and a second end adjacent to the outer surface of the conductive header; and
an electronic layer comprising a substrate and an electronic component disposed on or within the substrate, wherein the electronic component is electrically connected to the contact of the conductive header so that the electronic component is electrically connected to the conductive header, and further wherein a major surface of the substrate of the electronic layer faces the conductive inner surface of the conductive header without any intervening nonconductive layers disposed between the major surface of the substrate and the conductive inner surface of the conductive header so that a gap is formed between the electronic layer and the conductive header.

2. The module of claim 1, further comprising a conductive pad disposed at the first end of the feedthrough pin and electrically connected to the feedthrough pin.

3. The module of claim 2, wherein the conductive pad is disposed within a recessed surface disposed in the inner surface of the conductive header, wherein the conductive pad is electrically isolated from the header by a nonconductive layer disposed between the conductive pad and the recessed surface.

4. The module of claim 3, wherein the nonconductive layer comprises a ceramic disk.

5. The module of claim 3, wherein the nonconductive layer is disposed between the conductive pad and one or more side portions of the recessed surface.

6. The module of claim 1, further comprising a header electronic device disposed at the first end of the feedthrough pin and electrically connected to the feedthrough pin.

7. The module of claim 1, further comprising a second feedthrough pin disposed within a second via that extends through the header between the inner surface and the outer surface of the header, wherein the second feedthrough pin is electrically isolated from the header and comprises a first end adjacent to the inner surface of the header and a second end adjacent to the outer surface of the header.

8. The module of claim 1, further comprising a capacitor disposed within the via of the header, wherein the capacitor is electrically connected to the feedthrough pin and the header.

9. The module of claim 1, further comprising insulating material disposed within the via between a wall portion of the via and the feedthrough pin.

10. An implantable medical device comprising:
a power source; and
an electronics module electrically connected to the power source and comprising an electronic layer and a feedthrough header assembly electrically connected to the electronic layer, wherein the electronic layer comprises a substrate and an electronic component disposed on the substrate, wherein the feedthrough assembly comprises:
  a conductive header comprising a conductive inner surface, an outer surface, and a contact disposed on the inner surface and electrically connected to the header; and
  a feedthrough pin disposed within a via that extends through the header between the inner surface and the outer surface of the header, wherein the feedthrough pin is electrically isolated from the header and comprises a first end adjacent to the inner surface of the header and a second end adjacent to the outer surface of the header;
wherein the electronic component is connected to the contact of the conductive header so that the electronic component is electrically connected to the header, and further wherein a major surface of the substrate of the electronic layer faces the conductive inner surface of the header without any intervening nonconductive layers disposed between the major surface of the substrate and the conductive inner surface of the header so that a gap is formed between the electronic layer and the conductive header.

11. The device of claim 10, further comprising an elongated tubular housing extending between a first end and a second end along a longitudinal axis, and further wherein a first portion of the housing adjacent to the first end encloses the electronics module and a second portion of the housing adjacent to the second end encloses the power source.

12. The device of claim 11, wherein the first portion of the elongated tubular housing comprises a substantially transparent material.

13. The device of claim 11, wherein the longitudinal axis is substantially orthogonal to the substrate of the electronic layer of the electronics module.

14. The device of claim 10, further comprising a capacitor disposed within the via of the header, wherein the capacitor is electrically connected to the feedthrough pin and the header.

15. The device of claim 10, further comprising insulative material disposed within the via between a wall portion of the via and the feedthrough pin.

16. The device of claim 10, wherein the first end of the feedthrough pin is electrically connected to the power source.

17. A method comprising:
disposing a feedthrough pin through a via of a conductive header, wherein a first end of the feedthrough pin is adjacent to a conductive inner surface of the header and a second end of the feedthrough pin is adjacent to an outer surface of the header;
disposing a contact on the inner surface of the header so that it is electrically connected to the header; and
electrically connecting an electronic component of an electronic layer to the contact so that the electronic component is electrically connected to the header, wherein the electronic component is disposed on or within a substrate of the electronic layer, and further wherein a major surface of the substrate of the electronic layer faces the conductive inner surface of the header without any intervening nonconductive layers disposed between the major surface of the substrate and the conductive inner surface of the header so that a gap is formed between the electronic layer and the conductive header.

18. The method of claim 17, wherein disposing the contact on the inner surface of the header comprises:
disposing a seed layer on the conductive inner surface of the conductive header;
disposing a conductive layer on the seed layer;
patterning the conductive layer and the seed layer; and
disposing a solder ball on the patterned conductive layer.

19. The method of claim 17, further comprising electrically connecting the electronic layer to the feedthrough pin.

20. The method of claim 17, further comprising removing a portion of the feedthrough pin adjacent to the inner surface of the conductive header so that an end surface at the first end of the feedthrough pin is in a plane defined by the inner surface of the conductive header.

* * * * *